US005538717A

United States Patent [19]
La Poterie

[11] Patent Number: 5,538,717
[45] Date of Patent: Jul. 23, 1996

[54] AQUEOUS NAIL POLISH CONTAINING AS FILM-FORMING SUBSTANCE PARTICLES OF POLYESTER-POLYURETHANE WHICH ARE ANIONIC IN DISPERSION

[75] Inventor: Valérie de La Poterie, Le Chatelet En Brie, France

[73] Assignee: L'Oreal, Paris, France

[21] Appl. No.: 323,225

[22] Filed: Oct. 14, 1994

[30] Foreign Application Priority Data

Oct. 15, 1993 [FR] France ................................. 93 12272

[51] Int. Cl.⁶ ......................................................... A61K 7/04
[52] U.S. Cl. .......................... 424/61; 424/401; 424/485; 424/486; 424/489; 424/500; 424/501; 524/507; 524/589; 524/590; 525/424; 525/454; 525/457; 525/460
[58] Field of Search ............................. 424/61, 401, 485, 424/486, 489, 500, 501; 524/507, 589, 590; 525/424, 454, 457, 460

[56] References Cited

U.S. PATENT DOCUMENTS

| | | | |
|---|---|---|---|
| 4,526,913 | 7/1985 | Winkler et al. | 524/31 |
| 4,943,462 | 7/1990 | Konerska et al. | 424/61 |
| 5,102,654 | 4/1992 | Castrogiovanni et al. | 424/61 |
| 5,114,485 | 5/1992 | Lynch et al. | 106/311 |
| 5,120,529 | 6/1992 | Koch et al. | 424/61 |
| 5,318,619 | 6/1994 | Lynch et al. | 524/43 |
| 5,369,163 | 11/1994 | Chiou et al. | 524/460 |

FOREIGN PATENT DOCUMENTS

| | | |
|---|---|---|
| 0143480 | 6/1985 | European Pat. Off. . |
| 0391322 | 10/1990 | European Pat. Off. . |
| 0423471 | 4/1991 | European Pat. Off. . |

*Primary Examiner*—John C. Bleutge
*Assistant Examiner*—Randy Gulakowski
*Attorney, Agent, or Firm*—Cushman Darby & Cushman

[57] ABSTRACT

Colored or colorless aqueous nail polish containing particles of polyester-polyurethane which are anionic in dispersion, and in which the particle size is between 2 and 40 nm, and the hardness (as measured using a Persoz' clock) of the film produced after drying for 24 hours at 30° C. and 50% relative humidity from a 300 μm-thick layer of an aqueous dispersion of said particles containing 28% dry matter is between 50 and 300 seconds.

16 Claims, No Drawings

AQUEOUS NAIL POLISH CONTAINING AS FILM-FORMING SUBSTANCE PARTICLES OF POLYESTER-POLYURETHANE WHICH ARE ANIONIC IN DISPERSION

The present invention concerns a cosmetic composition produced as a colored or colorless, aqueous nail polish containing, as film-forming substance, particles of a polyester-polyurethane which is anionic in dispersion, the size of said particles being between 2 and 40 nm.

At present, most compositions in the form of nail polishes have as their base a mixture of organic solvents containing nitrocellulose, an aryl-sulfonamide formaldehyde resin, or an alkyd resin and a plasticizing agent. By virtue of the presence of organic solvents, these polishes exhibit a number of disadvantages, since they may damage the nails or cuticles; moreover, they may pose certain dangers for their users when applied or as they dry. In addition, they may pose flammability risks.

Accordingly, research has focused for several years on perfecting nail polishes free of organic solvents, and, in particular, on aqueous polishes.

To this end, different film-forming substances have been considered.

Patent Application No. EP 143,480 describes the use in nail polishes of polyurethane dispersions. The only example of polyurethane dispersions described in EP 143,480 is a dispersion marketed under the trade name NEOREZ R 974® by the ICI Company wherein the particle size is 68 nm.

In addition, Patent Application No. EP 423,471 described the use of polyurethane-polyurea dispersions in which the particle size was less than 200 nm.

However, it has emerged that the aqueous nail polishes produced from these dispersions were insufficiently remanent in water; that is, they tended to be removed simply by washing the hands in water.

After numerous studies, it has now been found that it is possible to significantly improve the durability in water of the aqueous nail polishes by using, as film-forming substances, dispersions of polyester-polyurethane particles, in which particle size ranges from 2 to 40 nm, while preserving entirely satisfactory gloss and spreadability of the polish over the nail surface.

Therefore, the present invention concerns a new industrial product which is a colored or colorless aqueous nail polish characterized by the fact that this polish contains particles of a polyester-polyurethane which is anionic in dispersion and in which the particle size ranges from 2 to 40 nm and the hardness, as measured using the Persoz' clock, of the film obtained after drying for 24 hours at 30° C. and at 50% relative humidity a layer 300 μm thick of an aqueous dispersion of said particles containing 28% dry matter is between 50 and 300 seconds.

In accordance with the invention, particle size was determined using a device marketed under the trade name BI-90> by the Brookhaven Instruments Corporation.

The size of the particles used in the nail polishes according to the invention is preferably between 2 and 30 nm.

Hardness was determined using the so-called Persoz' clock method and is specified in Standard NF-T-30-016.

Hardness, as previously specified, preferably ranges between 80 and 250 seconds.

According to a preferred embodiment of the nail polishes specified by the invention, the proportion of the polyester-polyurethane particles in the dispersion is between 3 and 50%, and preferably between 10 and 50%, of the total weight of the polish.

The polyester-polyurethane particles used according to the invention are normally sold as aqueous dispersions.

The proportion of polyester-polyurethane particles in these dispersions currently available on the market is between approximately 30 and 50% by weight of the total weight of the dispersion.

The anionic polyester-polyurethane dispersions that can be used in the aqueous nail polishes according to the invention include, in particular, those marketed under the trade names SANCURE 2060® and SANCURE 815® by the Sanncor Company.

According to another embodiment of the aqueous nail polishes according to the invention, the polishes further contain particles of anionic polyether-polyurethane in dispersion, in which the particle size is between 30 and 500 nm, and preferably between 50 and 150 nm.

The proportion of polyether-polyurethane particles in dispersion is normally lower than that of the polyester-polyurethane particles.

The polyether-polyurethane particles are also sold as aqueous dispersions.

Among the polyether-polyurethane particle dispersions, use is preferably made of those in which the film produced after drying possesses a surface energy of between 15 and 45 mg/m², as measured by the angle-of-contact method.

The angle-of-contact method consists of placing a drop of water and a drop of diidomethane on this film followed by measurement of the angle formed by each drop and the film, and then calculating the surface energy of the film in accordance with the method described in *Couble liaison—Chim. Peint* 82, Vol. 29, pp. 263 to 268.

Among the dispersions of anionic polyether-polyurethane particles suitable for the invention, mention can be made of those sold under the trade name SANCURE 878® by the Sanncor Company and NEOREZ R 970® by the ICI Company.

The anionic nature of the polyester-polyurethane and of the polyether-polyurethanes used in accordance with the invention results from the presence of carboxylic or sulfonic acid function groups in the units composing them.

According to another embodiment of the nail polishes according to the invention, use may be made of a mixture of commercial dispersions composed of anionic polyester-polyurethane particles, as described above, and of anionic polyether-polyurethane particles, also described above.

For example, it is possible to use a mixture comprising the dispersion sold under the trade name SANCURE 2060® and the dispersion sold under the trade name SANCURE 861®; or a mixture of the dispersion sold under the name SANCURE 815® and that sold under the name SANCURE 878®. These dispersions are sold by the Sanncor Company. According to the invention, preference is given to mixtures containing 60% to 70% polyester-polyurethane particles, the remainder being comprised of polyether-polyurethane particles.

The nail polishes according to the invention may also contain at least one thickening agent in a proportion of from 0.01% to 5%, and preferably between 0.1% and 1%, by weight of the total weight of the polish.

Thickening agents proving suitable for the aqueous nail polish formulation include cellulose and the derivatives thereof, such as carboxymethylcellulose and hydroxyethylcellulose, silicates, clays such as laponite, synthetic polymers such as acrylic or associative polyurethane-type polymers, and natural gums, such as carrageenan or xanthane gum. A thickening agent chosen from among hydroxyethylcellulose, laponite, and the associative polyurethanes is preferably selected.

When the nail polishes according to the invention are colored, they then contain at least one organic or inorganic pigment in a proportion of between 0.01% and 5% by weight, and preferably between 0.5% and 2% by weight of the total weight of the polish.

Organic pigments include D and C Red, Nos. 10, 11, 12 and 13, D and C Red No. 7, D and C Red Nos. 5 and 6, D and C Red Nos. 30 and 34, lacquers such as D and C Yellow No. 5 and D and C Red No. 2, or guanine.

The group of inorganic pigments comprises titanium dioxide, bismuth oxychloride, brown iron oxide, and the red iron oxides.

Moreover, it is possible to adjust the spreadability of the polishes by using water-soluble fluorinated surfactants, including, in particular, those corresponding to formulae (I), (II) and (III), below:

1) $(C_nF_{2n+1})$—$C_2H_4X$+tm (I)

wherein the radical $C_nF_{2n+1}$ is linear or branched, n is between 3 and 16,

X is a radical chosen from among:

(i) —$CO_2Y$, (ii) —$SO_3Y$, Y being an atom of hydrogen, an alkaline metal or an amine group, such as an ammonium group, (iii) —$(OC_2H_4)_m$—OH, m being between 2 and 100, and preferably between 4 and 40.

(iv) 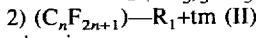

(v) —$SO_2NH(CH_2)_3$—$N\oplus(CH_3)_3I\ominus$, (vi) 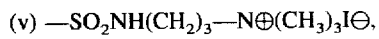

(vii) 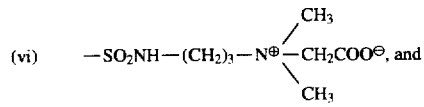

(viii) —$SCH_2CH_2R$, R being either the radical $CO_2M$, M being an alkaline metal, especially lithium; or the radical $N\oplus(CH_3)_3CH_3SO_4\ominus$.

2) $(C_nF_{2n+1})$—$R_1$+tm (II)

wherein:

the radical $C_nF_{2n+1}$ is linear or branched, n being between 4 and 16, $R_1$ is a radical chosen from among:

$SO_3\ominus NH_3\oplus$, $CO_2\ominus NH_4\oplus$, $SO_3\ominus N\oplus(R_3)_4$, and $CO_2\ominus N\oplus(R_3)_4$, $R_3$ being an alkyl radical of $C_1$–$C_4$ or $R_1$ is a radical corresponding to one of the following formula:

(i) —$SO_2N(R_3)CH_2$—$CO_2\ominus X\oplus$ wherein $R_3$ is as specified above, and X is an atom of hydrogen or an alkaline metal, (ii) —$SO_2$—$NH(CH_2)_pN\oplus(R_3)_3$ $I\ominus$ p being a whole number between 1 and 4, and $R_3$ corresponds to $R_3$ as specified above, and (iii) —$SO_2$—$N(R_3)(CH_2CH_2OY)$ Y being an atom of hydrogen or an alkyl radical of $C_1$–$C_4$, and $R_3$ corresponds to $R_3$ as specified above.

$(C_nF_{2n+1}C_2H_4O)_xP(O)$ $(R)_y$+tm (III)

wherein n being between 3 and 8, x and y, which are different, are 1 or 2, and

R is $ONH_4$ or OH.

The perfluoroalkyl compounds according to formula (I) include those corresponding to the following formulae:

a) 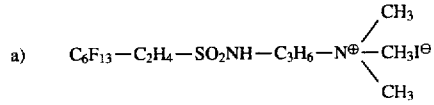

sold under trade name FORAFAC 1179® by the Atochem Company;

b) 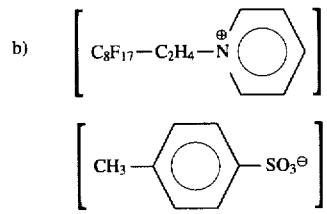

sold under the trade name FORAFAC 1098® by the Atochem Company;

c) 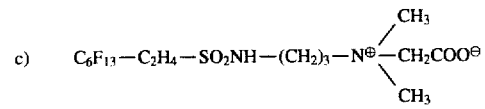

sold under the trade name FORAFAC 1157® by the Atochem Company;

d) $C_nF_{2n+1}CH_2CH_2O(CH_2CH_2O)_xH$ wherein n=3 to 8, and x=2 to 100, sold under the trade names ZONYL-FSN® and ZONYL-FSN 100® by the DuPont company;

e) $C_nF_{2n+1}CH_2CH_2SCH_2CH_2CO_2Li$ wherein n=3 to 8 sold under the trade name ZONYL FSA® by the Dupont Company; and f) $C_nF_{2n+1}CH_2CH_2SCH_2CH_2N\oplus(CH_3)_3CH_3SO_4\ominus$ wherein n=3 to 8 sold under the trade name ZONYL FSC® by the DuPont Company.

The perfluoroalkyl compounds corresponding to formula (II) include, in particular:

a) $C_nF_{2n+1}SO_2N(C_2H_5)CH_2CO_2\ominus$ $K\oplus$ wherein n=8 sold under the trade name FLUORAD FC 129® by the 3M Company;

b) $C_nF_{2n+1}SO_2NHC_3H_6N\oplus(CH_3)_3I\ominus$ wherein n=8 sold under the trade name FLUORAD FC 135® by the 3M Company;

c) $C_nF_{2n+1}SO_2N(C_2H_5)(CH_2CH_2OH)$ wherein n=8 sold under the trade name FLUORAD FC 170C by the 3M Company;

d) $C_nF_{2n+1}SO_3^{\ominus}NH_4^{\oplus}$ wherein n=10 sold under the trade name FLUORAD FC 120® by the 3M Company;

e) $C_nF_{2n+1}SO_2N(C_2H_5)CH_2CO_2^{\ominus}NH_4^{\oplus}$ wherein n=8 sold under the trade name FLUORAD FC 143® by the 3M Company.

The perfluoroalkyl compounds corresponding to formula (III) include, in particular:

a) $(C_nF_{2n+1}CH_2CH_2O)_{1-2}P(O)(ONH_4)_{2-1}$ wherein n=3 to 8 sold under the trade name ZONYL FSP®, PSE® by the DuPont Company; and b) $(C_nF_{2n+1}CH_2CH_2O)_{1-2}P(O)(OH)_{2-1}$ wherein n=3 to 8 sold under the trade name ZONYL UR® by the DuPont Company.

The proportion of water-soluble fluorinated surfactants may be between 0.01 and 1% by weight, and preferably between 0.05 and 0.2% by weight, of the total weight of the nail polish.

The nail polishes according to the invention may further contain at least one additive selected from among a wetting agent, a dispersing agent, an anti-foaming agent, a sunscreen, a preservative, a drying-acceleration agent, a wax, a silicone, or a mixture thereof.

We will now provide as illustrations several examples of aqueous nail polishes according to the invention.

EXAMPLE 1: COLORED NAIL POLISH

| | |
|---|---|
| Aqueous 30% dispersion of anionic polyester-polyurethane sold under the trade name SANCURE 2060 ® by the Sanncor Company | 93.3% |
| Associative polyurethane thickening agent sold under the trade name SER AD FX 1100 ® by the Servo Company | 0.30% |
| Pigments | 1% |
| Preservatives | 0.05% |
| Water qsp | 100% |

The polish obtained spread easily on the nail and, after drying, gave a very satisfactory hardness.

Water-resistance of the polish obtained was analyzed by applying a 300 μm film on a glass plate, then by immersing it for one hour while stirring in cold or hot (45° C.) water, with or without detergent. No discoloration was then observed, nor were any tearing or dissolution of the film over time noted.

The polish obtained thus had excellent water-resistance, in particular to hot water, even in the presence of a detergent.

EXAMPLE 2: COLORED NAIL POLISH

| | |
|---|---|
| Aqueous 35% dispersion of anionic polyester-polyurethane sold under the trade name SANCURE 815 ® by the Sanncor Company | 85.7% |
| Associative polyurethane thickening agent sold under the trade name SER AD FX 1100 ® by the Servo Company | 0.30% |
| Pigments | 1% |
| Preservatives | 0.05% |
| Water qsp | 100% |

EXAMPLE 3: COLORED NAIL POLISH

| | |
|---|---|
| Aqueous 30% dispersion of anionic polyester-polyurethane sold under the trade name SANCURE 2060 ® by the Sanncor Company | 65.3% |
| 40% aqueous dispersion of anionic polyether-polyurethane sold under the trade name SANCURE 861 ® by the Sanncor Company | 21.0% |
| Associative polyurethane thickening agent sold under the trade name SER AD FX 1100 ® by the Servo Company | 0.30% |
| Pigments | 1% |
| Preservatives | 0.05% |
| Water qsp | 100% |

EXAMPLE 4: COLORED NAIL POLISH

| | |
|---|---|
| Aqueous 35% dispersion of anionic polyester-polyurethane sold under the trade name SANCURE 815 ® by the Sanncor Company | 56.0% |
| 38% aqueous dispersion of anionic polyether-polyurethane sold under the trade name SANCURE 878 ® by the Sanncor Company | 22.1% |
| Associative polyurethane thickening agent sold under the trade name SER AD FX 1100 ® by the Servo Company | 0.30% |
| Pigments | 1% |
| Preservatives | 0.05% |
| Water qsp | 100% |

The polish obtained exhibited, after drying, very satisfactory hardness and water-resistance.

EXAMPLE 5: COLORED NAIL POLISH

| | |
|---|---|
| Aqueous 30% dispersion of anionic polyester-polyurethane sold under the trade name SANCURE 2060 ® by the Sanncor Company | 93.3% |
| Associative non-ionic polyurethane thickening agent sold under the trade name DAPRAL T 210 ® by the Akzo Company | 1.50% |
| Sodium and magnesium silicate sold under the trade name LAPONITE XLG ® by the Laporte Company | 0.20% |
| Fluorinated surfactant sold under the trade name FLUORAD FC-143 ® by the 3M Company | 0.10% |
| Pigments | 1.50% |
| Water qsp | 100% |

The polish produced spread easily on the nail and, after drying, exhibited very satisfactory hardness and water-resistance.

I claim:

1. A colored or colorless aqueous nail polish, wherein said nail polish comprises particles of anionic polyester-polyurethane in dispersion, and in which the particles' size is between 2 and 40 nm and the hardness, as measured using a Persoz' clock, of the film produced, after drying for 24 hours at 30° C. and 50% relative humidity, from a 300 μm-thick layer of an aqueous dispersion of said particles containing 28% dry matter is between 50 and 300 seconds.

2. The nail polish of claim 1 wherein said size of said particles is between 2 and 30 nm.

3. The nail polish of claim 1 wherein said hardness is between 80 and 250 seconds.

4. The nail polish of claim 1 wherein the proportion of said polyester-polyurethane particles in dispersion in said nail polish is between 3 and 50 percent by weight of the said polish.

5. The nail polish of claim 1 wherein the proportion of polyester-polyurethane particles in dispersion in said nail polish is between 10 and 50 percent by weight of the total weight of said nail polish.

6. The nail polish of claim 1 wherein said nail polish also contains particles of an anionic polyether-polyurethane in dispersion, the size of said particles being between 30 and 500 nm.

7. The nail polish of claim 1 wherein said polish also contains particles of an anionic polyether-polyurethane in dispersion, the size of said particles being between 50 and 150 nm.

8. The nail polish of claim 6 wherein the proportion by weight of said polyether-polyurethane particles is less than that of said polyester-polyurethane particles.

9. The nail polish of claim 1 wherein said nail polish additionally contains a thickening agent in a proportion between 0.01 and 5 percent by weight of the total weight of said nail polish.

10. The nail polish of claim 1 wherein said nail polish additionally contains a thickening agent in a proportion between 0.01 and 1 percent by weight of the total weight of said nail polish.

11. The nail polish of claim 9 wherein said thickening agent is selected from the group consisting of carboxymethyl-cellulose, hydroxyethylcellulose, silicate, clays, acrylic polymers, polyurethane polymers and natural gums.

12. The nail polish of claim 9 wherein said thickening agent is selected from the group consisting of hydroxyethylcellulose, laponite and polyurethane polymers.

13. The nail polish of claim 1 wherein said nail polish also contains an organic or inorganic pigment in a proportion of between 0.01 and 5 percent by weight of the total weight of said nail polish.

14. The nail polish of claim 1 wherein said nail polish also contains an organic or inorganic pigment in a proportion of between 0.5 and 2 percent by weight of the total weight of said nail polish.

15. The nail polish of claim 1 wherein said nail polish also contains a water-soluble fluorinated surfactant.

16. The nail polish of claim 1 wherein said nail polish also contains a member selected from the group consisting of a wetting agent, a dispersing agent, an anti-foaming agent, a sunscreen, a preservative, a drying-acceleration agent, a wax and a silicon.

* * * * *